United States Patent [19]

Takahashi

[11] Patent Number: 5,843,498
[45] Date of Patent: Dec. 1, 1998

[54] METHOD FOR DEPRESSING METHANOGENESIS IN THE RUMEN OF A RUMINANT

[75] Inventor: Junichi Takahashi, Obihiro, Japan

[73] Assignee: Snow Brand Seed Co., Ltd., Hokkaido, Japan

[21] Appl. No.: 921,711

[22] Filed: Sep. 2, 1997

Related U.S. Application Data

[63] Continuation of Ser. No. 458,840, Jun. 2, 1995, abandoned.

[30]     Foreign Application Priority Data

Jun. 2, 1994  [JP]  Japan .................................. 67-120877

[51] Int. Cl.⁶ .............................. A23K 1/18; A23L 1/305
[52] U.S. Cl. ................................................ 426/2; 426/807
[58] Field of Search ................................ 426/2, 656, 807

[56] References Cited

U.S. PATENT DOCUMENTS 3,949,090   4/1976   Chalupa et al. ............................ 426/2

OTHER PUBLICATIONS

Takahashi et al, "Prophylactic effect of L–cysteine on nitrate–induced alterations in respiratory exchange and metabolic rate in sheep", Animal Feed Science and Technology; 35(1991) 105–113.

Takahashi et al, EAAP publication, vol. 76, pp. 387–390, Sep. 1994.
Database WPI, Derwent Publications Ltd., London, GB; AN 94–080686 (Nov. 15, 1993).
Patent Abstracts of Japan, vol. 6, No. 49 (Dec. 17, 1981).
Patent Abstracts of Japan, vol. 15, No. 508 (Oct. 3, 1991).
H. Morimoto, (1985), Feed, Youkendo, Japan, pp. 254–255.
R. Onodera et al., (1989), Livestorck Nutrition, Kawasima Shoten, p. 184.
C.J. Newbold et al., Journal of Applied Bacteriology, (1993), 75:129–134.
Energy Metabolism of Farm Animals, Proceeding of the 12th Symposium, Kartause Ittingen, Switzerland, 1–7, (1991), pp. 376–379.
Energy Matabolism of Farm Animals, Proceeding of the 13th Symposium, Spain, (1994), 18–24.
Proceeding of the Society of Nutrition Physiology, (1994) V.3, 25–30, pp. 1, 175, 177, 178, 179–180, 387–390.

*Primary Examiner*—Arthur L. Corbin
*Attorney, Agent, or Firm*—Birch, Stewart, Kolasch & Birch, LLP

[57] ABSTRACT

A ruminant feed composition for depressing rumen methanogenesis and improving feed efficiency, which is safe and does not adversely affect a ruminant, and a method for feeding the composition to a ruminant. As an effective component of the feed composition, cysteine and/or its salts are fed to a ruminant in an amount of 0.02 to 0.21 g sulfur equivalent/kg of metabolic body weight per day.

1 Claim, 3 Drawing Sheets

5,843,498

METHOD FOR DEPRESSING METHANOGENESIS IN THE RUMEN OF A RUMINANT

This application is a continuation of application Ser. No. 08/458,840 filed on Jun. 2, 1995, now abandoned.

BACKGROUND OF THE INVENTION

1. Field of the invention

This invention relates to a composition which is fed to a ruminant so that the methanogenesis in the rumen thereof is depressed and the feed efficiency is improved. The present invention also relates to a method for depressing the methanogenesis in the rumen of a ruminant and improving feed efficiency by the use of the composition.

2. Statement of the Prior Art

Methane gas is generated in the rumen of a ruminant, such as cattle, sheep, goat and the like, and emitted in the air in a large amount, and such methanogenesis (methane generation) has become a serious problem because methane is one of potent greenhouse gases contributing global warming. The methanogenesis means energy loss of feed which are taken by a ruminant. From this standpoint also, the rumen methanogenesis is not preferable. In a rumen, extremely various kinds of microorganisms exist and contribute to fermentation, resulting in the production of various metabolites. Methane is one of the metabolites, produced by methane-producing bacteria. On the other hand, propionic acid is also produced by rumen fermentation as a result of microbial fermentation of carbohydrates, and it is thought that the energy metabolism depends upon the amount of propionic acid produced. In detail, it is thought that energy utilization efficiency depends upon the final position, namely, propionic acid or methane, to which electron generated by the oxidation of energy source in a rumen is transferred. Conventionally, it has been known that an ionophore antibiotic, such as monensin and salinomycin, coordinates the flow of electrons so that the rumen methane production is depressed and the propionic acid production is increased, and recently, the ionophore antibiotic is widely used for growing beef cattle. It is reported that the use of an ionophore antibiotic brings about 10% increase of the feed efficiency of a ruminant ("FEED, Revised", 1985, edited by Hiroshi Morimoto, published by Youkendo, Japan, pp.254–255; Ryoji Onodera et al.,"Livestock Nutrition", 1989, published by Kawasima Shoten, p.184).

However, since the ionophore such as monensin and salinomycin is an antibiotic, it has an adverse effect such that it depresses the activities of not only methane-producing bacteria but also the other rumen microorganisms. Therefore, attention should be drawn to the dosage so that essential rumen microorganisms may not be damaged. Further, there is a problem that even though an ionophore antibiotic is initially effective, the methane-producing bacteria in a rumen attain resistance to the ionophore antibiotic with the lapse of time. Cross-resistance between the antibiotics is another problem in the practice as feed additives (C. J. Newbold et al., Journal of Applied Bacteriology, 1993, 75:129–134).

SUMMARY OF THE INVENTION

The present inventor has made extensive and intensive studies with a view to depressing the rumen methanogenesis effectively without the above-mentioned problems. To this end, the inventor has examined various chemical compounds as a feed additive. As a result, the present inventor has surprisingly found that when a specific amino acid, cysteine, is fed to a ruminant, not only rumen methanogenesis, but also oxygen consumption, carbon dioxide gas production and propionic acid production, one of volatile fatty acids (VFA), are markedly depressed, contributing to the increase of feed efficiency. The present invention has been made based on such a novel finding.

Therefore, it is an object of the present invention to provide a novel ruminant feed composition which is excellent in depressing the rumen methanogenesis and increasing feed efficiency.

It is another object of the present invention to provide a method for effectively depressing rumen methanogenesis and improving feed efficiency of a ruminant.

The foregoing and other objects are achieved by providing a ruminant feed composition for feeding a ruminant to depress methanogenesis in the rumen thereof and improving feed efficiency, which comprises at least one substance selected from cysteine and its salts, and also achieved by a method which comprises feeding at least one substance selected from cysteine and its salts to a ruminant in an amount of 0.02 to 0.21 g sulfur equivalent/kg body weight$^{-0.75}$ per day as a total of said at least one substance.

DETAILED DESCRIPTION OF THE INVENTION

Figure 1:
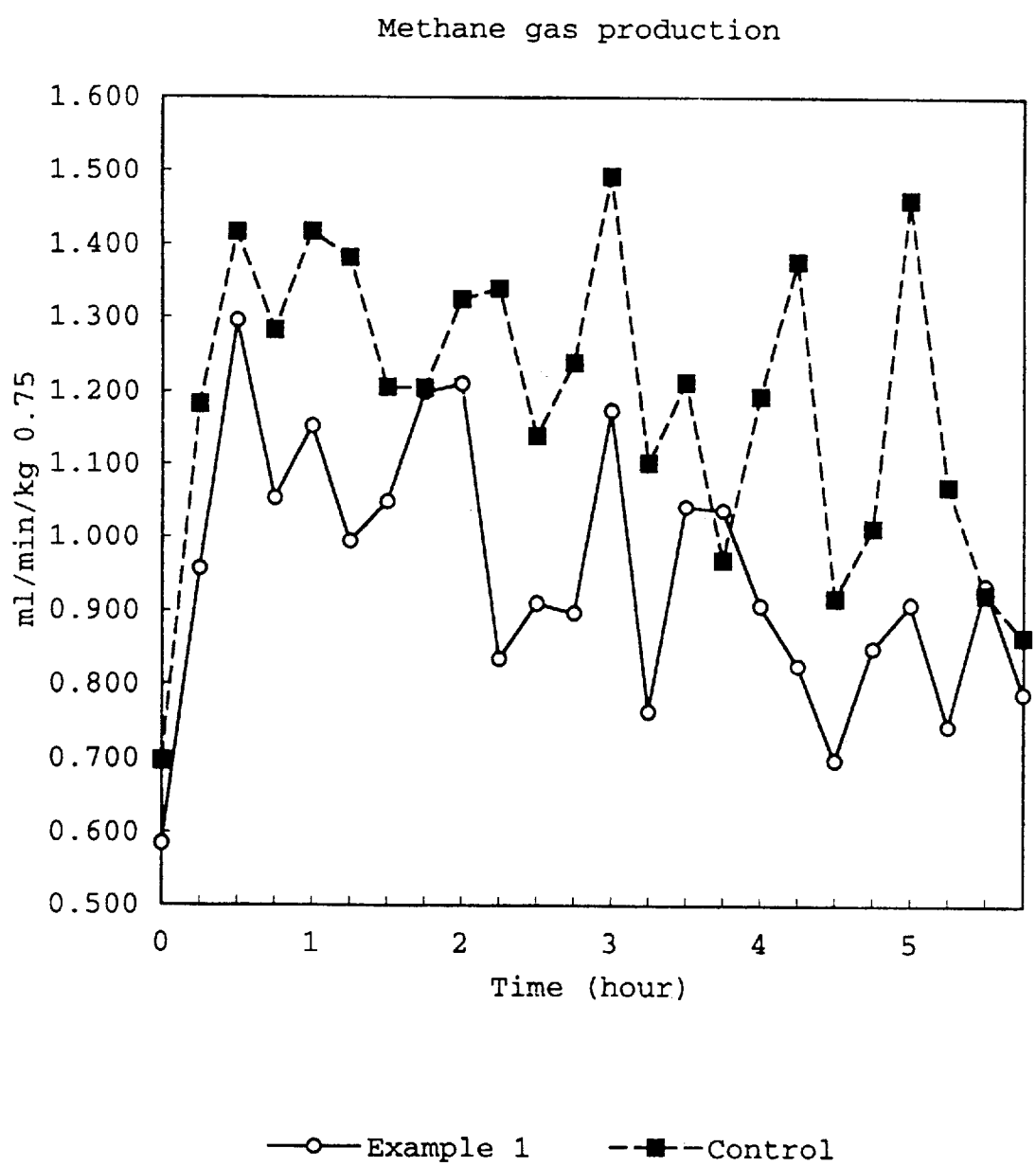
FIG. 1 is a graph showing the effect of the ruminant feed composition of the present invention on the depression of rumen methanogenesis.

In accordance with the present invention, there is provided a ruminant feed composition for feeding a ruminant to depress methanogenesis in the rumen thereof and improving feed efficiency, which comprises at least one substance selected from cysteine and its salts.

The ruminant feed composition of the present invention comprises at least one substance selected from cysteine and its salts. As the cysteine and its salts, any optical isomers, that is, L-, D- and DL-isomers, may be mentioned in the present invention.

As the salts of cysteine, there may be mentioned any salts which can be fed to a ruminant. For example, there may be mentioned cysteine hydrochloride, but not restricted thereto. There is no difference in the effect of methanogenesis depression and feed efficiency improvement between cysteine and its salts. However, cysteine is easily oxidized to cystine that is less effective than cysteine. Therefore, a salt of cysteine is more advantageous as compared to cysteine from the standpoint of protection from oxidation, namely, stability and storage.

With respect to the amount of cysteine and its salts, when the content in the feed composition of the present invention is high, the feeding amount can be decreased. On the other hand, when the content is low, the feeding amount can be increased. Therefore, the content of cysteine and its salts in the present invention is not limited. However, for feeding cysteine and its salts to a ruminant in an appropriate amount uniformly, it is preferred that the feed composition of the present invention be fed to a ruminant in an amount of about 50 g to about 1 kg daily. On the other hand, the daily amount of cysteine and its salts to be fed to a ruminant is 10 to 100 g, preferably 25 to 50 g per animal in terms of cysteine weight. Accordingly, the content of cysteine and its salts in the feed composition of the present invention is 1 to 100% in terms of cysteine content.

The cysteine and its salts contained in the feed composition of the present invention in an amount as mentioned above may be identified, for example, by the Folin-Chiocalteu method, mercury method and the like. The analytical method is described in, for example, "Handbook of Analytical Chemistry" (Bunsekikagaku Benran), edited by Japanese Society of Analytical Chemistry, published by Maruzen Co., Ltd., Japan, pp.1281–1288.

As the component of the feed composition of the present invention other than cysteine and its salts, there may be mentioned substrate materials which are generally used as a feed composition of ruminant feeds. As the representative examples of such substrate materials, there may be mentioned wheat bran, rice bran, corn meal, cereal grains such as barley, wheat, rye and oat, soybean meal, alfalfa meal, wheat powder, and the like. The shape of feed composition of the present invention is not restricted and may be in any form of a conventional feed composition, such as a powder and a pellet. The feed composition of the present invention may be produced according to the generally employed method for producing a compound feed and a feed supplement. For example, the present feed composition may be produced by a method comprising a premixing step in which cysteine and its salts are mixed with a small amount of a substrate material to prepare a premix; a mixing step in which the premix is combined with the remaining large amount of the substrate material; and a finishing step comprising a process of supplementing liquid materials, a granulating process and a pelleting process. Such a method is described in, for example, "Lecture on Compound Feed" (Haigoshiryou Koza), the second volume, published by Chikusan Shuppansha, Japan, pp.15–27.

The feed composition of the present invention may also be formulated in the same form as a pharmaceutical composition for livestock. For example, it may be in the form of granules, tablets, pellets, capsules and the like. As components other than cysteine and its salts, in the case of granules, there may be mentioned carriers such as lactose, sodium hydrogen carbonate, sodium chloride, sucrose, mannitol, starch, crystalline cellulose, calcium sulfate, precipitated calcium carbonate and calcium phosphate; collapsing agents such as starch and crystalline cellulose; and binders such as an aqueous 10–20% gum arabic solution, an aqueous 5–10% starch solution, an aqueous or alcoholic 5–10% PVP solution and an aqueous or alcoholic 1–2% cellulose derivative solution. In the case of tablets, there may be mentioned, for example, carriers such as lactose, sucrose, glucose, starch and crystalline cellulose; binders such as an aqueous 5–10% starch solution, an aqueous hydroxypropyl cellulose solution, an aqueous carboxymethyl cellulose solution, an aqueous gum arabic solution, an aqueous tragacanth solution, an aqueous sucrose solution, an aqueous glucose solution and sodium alginate; collapsing agents such as starch and calcium carboxymethyl cellulose; and lubricants such as refined tarc, stearic acid, magnesium stearate and calcium stearate. In the case of pellets and capsules, there may be mentioned, in addition to the above mentioned carriers and binders, coating agents such as sucrose, starch, tarc and the like for pellets, and gelatin, glycerol, sorbitol and the like for capsules. The above-mentioned compositions may be produced according to the method generally employed for producing a pharmaceutical composition for livestock well known in the art. According to need, a stabilizing agent such as an antioxidant may be combined in the present feed composition.

By feeding the present feed composition to a ruminant, the rumen methanogenesis can be depressed and the feed efficiency can be improved. Accordingly, it is another object of the present invention to provide a method for depressing methanogenesis in the rumen of a ruminant and improving feed efficiency, which comprises feeding at least one substance selected from cysteine and its salts to a ruminant in an amount of 0.02 to 0.21 g sulfur equivalent/kg body weight$^{-0.75}$ per day as a total of said at least one substance. In the specification of the present application, "kg body weight$^{-0.75}$" means 1 kg of metabolic body weight.

The feeding amount is not restricted as long as the methanogenesis is efficiently depressed while the nutrient balance is not adversely affected. From the standpoint of cost and feed efficiency, it is preferred that the feeding amount of the total of cysteine and its salts be in the range of 0.02 to 0.21 g sulfur equivalent.kg body weight$^{-0.75}$ per day, more preferably 0.05 to 0.10 g sulfur equivalent/kg body weight$^{-0.75}$ per day. The upper limit of the feeding amount is the daily sulfur demand according to National Research Council (NRC) 1985, U.S.A. Therefore, even if cysteine and its salts are fed in an amount larger than the upper limit, the effect is not increased as compared to the cost increase. On the other hand, when the feeding amount is lower than the above-mentioned lower limit, it is possible that the rumen methanogenesis depression and feed efficiency become insufficient. In detail, in the case of, for example, a cattle having a body weight of 700 kg, the feeding amount of cysteine and its salts may be preferably 10 to 100 g, more preferably 25 to 50 g per animal per day in terms of cysteine weight. The manner of feeding is not restricted, and the feed composition of the present invention may be fed by top-dressing over the compound feed, or fed after the present feed composition is mixed with the compound feed.

Since the ruminant feed composition of the present invention comprises cysteine which is found in nature as a component of a protein, and/or salts thereof, it can be effectively and safely fed to a ruminant as compared to the ionophore antibiotics, such as monensin and salinomycin.

The present invention will now be described in more detail with reference to the following Example, which should in no way be construed to be limiting the scope of the present invention.

EXAMPLE 1

Two rumen-fisturated, adult sheep (Suffolk) wethers (No.1 and No.2) were individually caged in a controlled environment at 18° C. and 45% RH (relative humidity). Chopped grass hay of cocksfoot (*Dactylis glomerata*) was daily offered once a day at 8:00 a.m. in an amount of 55 g/kg body weight$^{-0.75}$. Simultaneously, cysteine was fed in an amount of 0.105 g sulfur equivalent/kg body weight$^{-0.75}$ per day. Water was freely available. On the eighth (8th) day from the initiation of administration, methane production, carbon dioxide production, oxygen consumption in rumen were determined at the time of administration of cysteine and thereafter continually at intervals of 15 minutes, and pH and VFA (volatile fatty acids) contents in rumen juice were determined 4 hours after the administration. The determination of methane production, carbon dioxide production, oxygen consumption in rumen was conducted in the following manner. Respiratory gas exchanges were monitored by means of an open-circuit respiratory system using a hood and face mask, by compulsorily ventilating the expiration of an animal by means of a blower and detecting the expiration volume by means of a dry gas meter. The pressure and temperature of the expiration, and the atmospheric pressure and temperature were measured at intervals of 30 minutes. The carbon dioxide concentration and methane concentration in the expiration were measured by means of an infrared spectrometer model VIA-500 (manufactured by HORIBA Co., Ltd., Japan) and oxygen concentration was measured by means of a magnetic oxygen analyzer model MAG-2 (manufactured by Shimadzu Corp., Japan). Each concentration measured was automatically input in a computer (PC-9801VM, manufactured by NEC, Japan) and calculated in terms of a value at 0° C. at 1 atom. The pH was measured by means of a pH meter model F-13 (manufactured by Hitachi-Horiba, Japan). The volatile fatty acids were measured according to the following method. 1.5 ml of a rumen juice sample was taken from the fistura, and centrifuged at 8,000x g for 5 minutes, thereby to obtain a supernatant. To 0.8 ml of the supernatant was added 0.2 ml of 25% methaphosphoric acid, followed by freezing overnight. Then, the resultant mixture was fused and centrifuged at 8,000x g for 5 minutes to obtain a supernatant. To 0.5 ml of the supernatant was added 1 ml of 10 mM 2-ethylbutyric acid as an internal standard (sample solution). A calibration agent was prepared in substantially the same manner as mentioned above except that a mixture of 50 mM acetic acid, 50 mM propionic acid, 10 mM isobutyric acid, 50 mM butyric acid, 10 mM isovalerianic acid, 10 mM valerianic acid, 5 mM isocaproic acid and 5 mM caproic acid was used instead of a rumen juice sample. The VFA concentration was analyzed by means of a gas chromatography model CG-14A (manufactured by Shimadzu Corp., Japan) and calculated by means of an automatically calculating program (Chromato-Pack, manufactured by Shimadzu Corp., Japan).

On the other hand, as a control, No.2 animal was fed in substantially the same manner as mentioned above except that cysteine is not fed.

Figure 2:
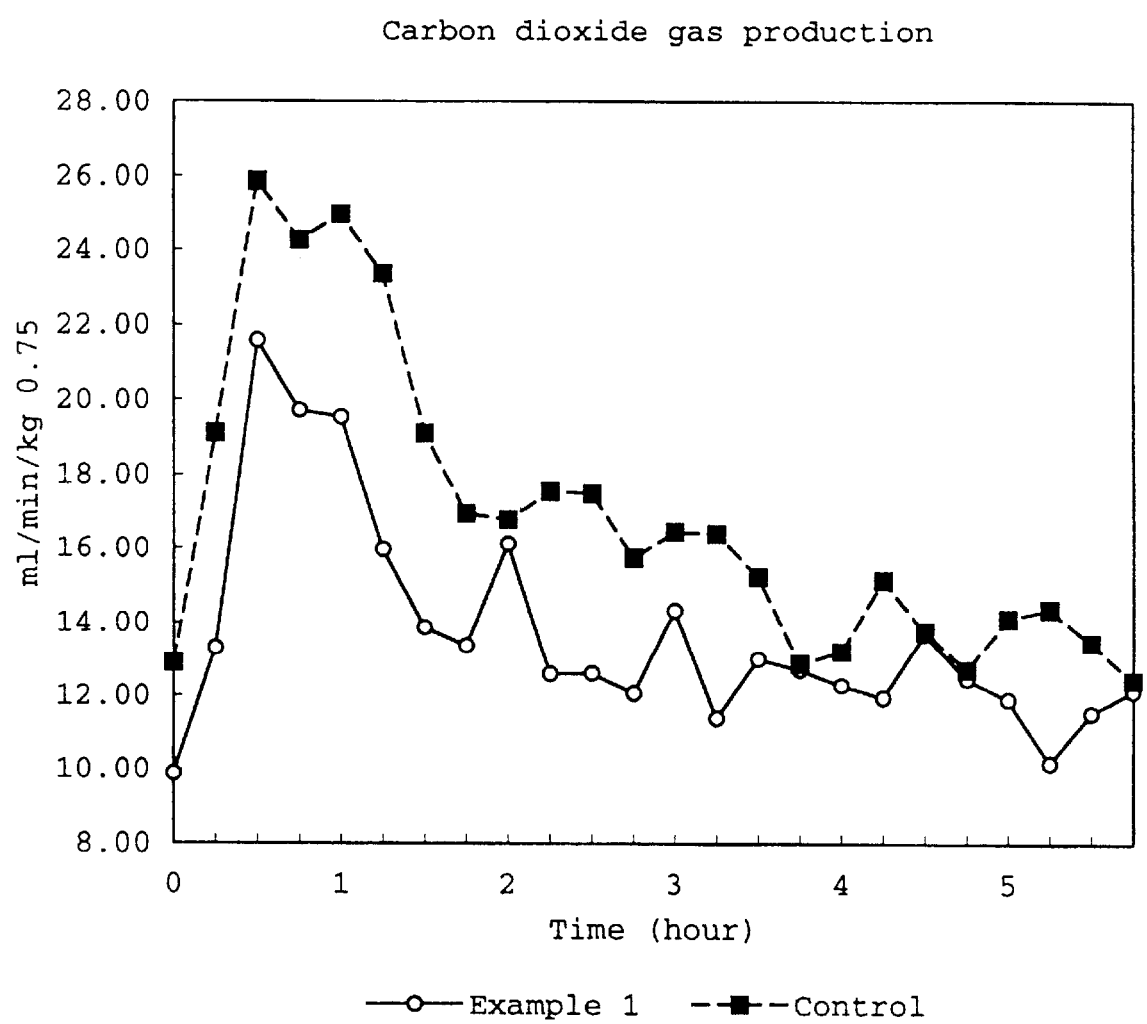
FIG. 2 is a graph showing the effect of the ruminant feed composition of the present invention on the depression of carbon dioxide production in a rumen.
Figure 3:
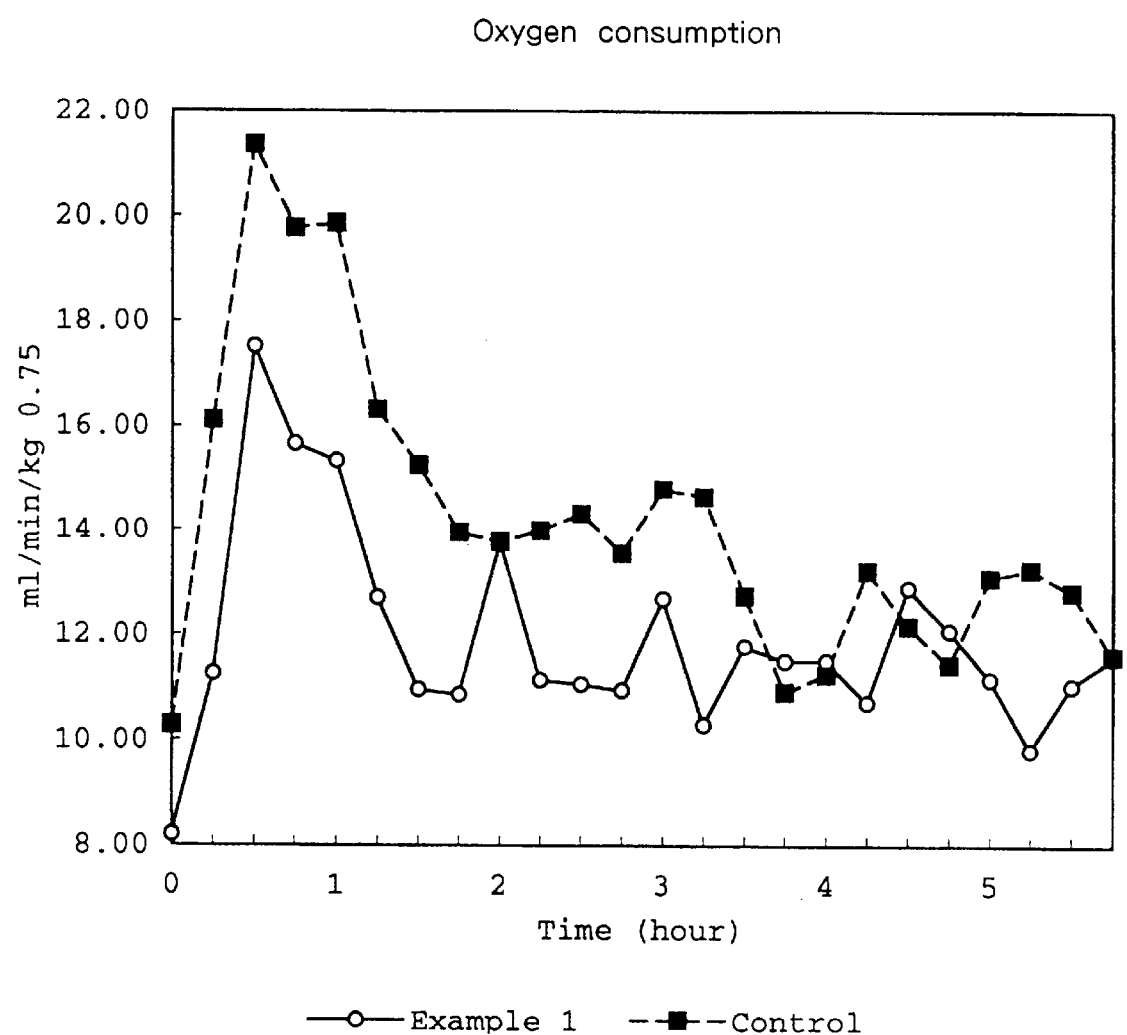
FIG. 3 is a graph showing the effect of the ruminant feed composition of the present invention on the depression of oxygen consumption in a rumen.

From the ninth (9th) day of the initiation, the feed was exchanged between the No.1 and No.2 sheeps, followed by the measurement in the same manner as mentioned above. This exchange was further repeated so that the measurement was conducted in 3 repetitions in total. The average and standard deviation were calculated with respect to each item. The results are shown in Tables 1, 2, 3 and 4 and FIGS. 1, 2 and 3.

As apparent from the results shown in the Tables and Figs, the rumen methanogenesis was markedly depressed by the feeding of cysteine. This exhibits that the energy loss resulting from methanogenesis was depressed. Further, the carbon dioxide production and oxygen consumption were also depressed. These results exhibit that the heat increment (the sum of maintenance energy increment and production energy increment) was depressed, that is, the feed efficiency (energy efficiency of feed that a ruminant has taken) has been increased.

The pH value was not changed by the feeding of cysteine. On the other hand, with respect to the VFA content, the propionic acid content was decreased while the acetic acid content was increased. It is known that the conventionally used ionophore antibiotic, such as monensin and salinomycin, increases the propionic acid content. Therefore, it seems that cysteine affects the rumen methanogenesis in a manner different from the case of ionophore antibiotic.

TABLE 1

Methane gas production

| Time (hour) | Example 1 ml/min/kg 0.75 | Control |
|---|---|---|
| 0 | 0.585 ± 0.394 | 0.697 ± 0.133 |
|   | 0.957 ± 0.331 | 1.183 ± 0.145 |
|   | 1.296 ± 0.028 | 1.417 ± 0.297 |
|   | 1.054 ± 0.314 | 1.283 ± 0.085 |
| 1 | 1.153 ± 0.419 | 1.418 ± 0.176 |
|   | 0.994 ± 0.374 | 1.382 ± 0.162 |
|   | 1.049 ± 0.453 | 1.206 ± 0.193 |
|   | 1.199 ± 0.361 | 1.205 ± 0.353 |
| 2 | 1.211 ± 0.260 | 1.325 ± 0.166 |
|   | 0.834 ± 0.305 | 1.340 ± 0.312 |
|   | 0.910 ± 0.196 | 1.140 ± 0.053 |
|   | 0.897 ± 0.275 | 1.240 ± 0.016 |
| 3 | 1.175 ± 0.370 | 1.493 ± 0.058 |
|   | 0.763 ± 0.131 | 1.102 ± 0.066 |
|   | 1.042 ± 0.192 | 1.213 ± 0.350 |
|   | 1.037 ± 0.259 | 0.968 ± 0.085 |
| 4 | 0.907 ± 0.326 | 1.194 ± 0.140 |
|   | 0.825 ± 0.364 | 1.377 ± 0.328 |
|   | 0.698 ± 0.364 | 0.917 ± 0.151 |
|   | 0.849 ± 0.344 | 1.013 ± 0.076 |
| 5 | 0.909 ± 0.203 | 1.461 ± 0.436 |
|   | 0.744 ± 0.160 | 1.070 ± 0.090 |
|   | 0.935 ± 0.562 | 0.923 ± 0.148 |
|   | 0.788 ± 0.494 | 0.865 ± 0.024 |

TABLE 2

Carbon dioxide gas production

| Time (hour) | Example 1 ml/min/kg 0.75 | Control |
|---|---|---|
| 0 | 9.87 ± 2.312 | 12.88 ± 3.127 |
|   | 13.29 ± 2.509 | 19.10 ± 6.248 |
|   | 21.59 ± 2.162 | 25.86 ± 1.342 |
|   | 19.70 ± 3.910 | 24.27 ± 1.756 |
| 1 | 19.53 ± 4.398 | 24.96 ± 1.866 |
|   | 15.96 ± 3.829 | 23.35 ± 2.895 |
|   | 13.85 ± 3.655 | 19.09 ± 3.171 |
|   | 13.36 ± 3.553 | 16.94 ± 4.466 |
| 2 | 16.12 ± 2.523 | 16.78 ± 0.818 |
|   | 12.59 ± 2.766 | 17.54 ± 3.359 |
|   | 12.60 ± 2.372 | 17.48 ± 3.150 |
|   | 12.05 ± 3.222 | 15.73 ± 2.307 |
| 3 | 14.31 ± 3.775 | 16.43 ± 1.970 |
|   | 11.37 ± 2.389 | 16.38 ± 2.013 |
|   | 12.99 ± 2.558 | 15.23 ± 2.332 |
|   | 12.69 ± 1.090 | 12.86 ± 1.908 |
| 4 | 12.27 ± 2.629 | 13.19 ± 1.302 |
|   | 11.93 ± 2.140 | 15.13 ± 3.040 |
|   | 13.68 ± 2.542 | 13.75 ± 1.878 |
|   | 12.43 ± 2.782 | 12.69 ± 1.982 |
| 5 | 11.88 ± 2.388 | 14.09 ± 0.673 |
|   | 10.15 ± 1.896 | 14.35 ± 2.222 |
|   | 11.51 ± 3.099 | 13.43 ± 1.936 |
|   | 12.11 ± 4.658 | 12.39 ± 1.688 |

TABLE 3

| Time (hour) | Oxygen consumption ml/min/kg 0.75 | |
|---|---|---|
| | Example 1 | Control |
| 0 | 8.20 ± 2.014 | 10.28 ± 1.591 |
| | 11.26 ± 1.043 | 16.12 ± 4.860 |
| | 17.52 ± 0.940 | 21.36 ± 1.246 |
| | 15.67 ± 2.348 | 19.78 ± 2.311 |
| 1 | 15.34 ± 2.423 | 19.86 ± 1.895 |
| | 12.71 ± 2.143 | 16.32 ± 3.368 |
| | 10.95 ± 2.101 | 15.26 ± 2.564 |
| | 10.85 ± 2.891 | 13.96 ± 3.762 |
| 2 | 13.76 ± 1.341 | 13.78 ± 0.474 |
| | 11.13 ± 2.421 | 13.99 ± 2.212 |
| | 11.05 ± 2.305 | 14.32 ± 1.929 |
| | 10.93 ± 2.204 | 13.55 ± 1.970 |
| 3 | 12.68 ± 2.459 | 14.79 ± 2.473 |
| | 10.28 ± 0.533 | 14.65 ± 2.364 |
| | 11.77 ± 0.952 | 12.74 ± 1.071 |
| | 11.49 ± 0.771 | 10.90 ± 1.292 |
| 4 | 11.49 ± 2.782 | 11.23 ± 0.514 |
| | 10.70 ± 0.948 | 13.21 ± 1.903 |
| | 12.89 ± 0.926 | 12.17 ± 0.803 |
| | 12.08 ± 1.844 | 11.42 ± 1.619 |
| 5 | 11.15 ± 1.120 | 13.08 ± 0.254 |
| | 9.80 ± 1.050 | 13.25 ± 1.944 |
| | 11.02 ± 2.166 | 12.81 ± 1.546 |
| | 11.55 ± 3.635 | 11.60 ± 1.560 |

TABLE 4

| | VFA content (mol %) and pH in a rumen juice | | | |
|---|---|---|---|---|
| | Acetic acid | Propionic acid | Butyric acid | pH |
| Control | 71.7 ± 0.12 | 20.07 ± 0.56 | 8.23 ± 0.59 | 6.46 ± 0.15 |
| Exmple 1 | 75.12 ± 0.76 | 16.55 ± 0.57 | 8.33 ± 0.31 | 6.31 ± 0.06 |

What is claimed is:

1. A method for depressing methanogenesis in the rumen of a ruminant and improving feed efficiency, which comprises feeding at least one substance selected from the group consisting of cysteine and its salts to a ruminant in a total amount of 0.02 to 0.1 g sulfur equivalent/kg of metabolic body weight per day.

* * * * *